(12) United States Patent
Thomas

(10) Patent No.: US 7,077,961 B2
(45) Date of Patent: Jul. 18, 2006

(54) APPARATUS FOR EXTRACORPOREAL BLOOD OR PLASMA TREATMENT COMPRISING A WET SEMI-PERMEABLE MEMBRANE AND METHODS FOR MAKING THE SAME

(75) Inventor: Michel Thomas, Serezin du Rhône (FR)

(73) Assignee: Hospal Industrie, Meyzieu (FR)

( * ) Notice: Subject to any disclaimer, the term of this patent is extended or adjusted under 35 U.S.C. 154(b) by 322 days.

(21) Appl. No.: 10/203,106

(22) PCT Filed: Dec. 3, 2001

(86) PCT No.: PCT/IB01/02297

§ 371 (c)(1),
(2), (4) Date: Aug. 6, 2002

(87) PCT Pub. No.: WO02/45830

PCT Pub. Date: Jun. 13, 2002

(65) Prior Publication Data
US 2003/0102262 A1 Jun. 5, 2003

(30) Foreign Application Priority Data
Dec. 18, 2000 (FR) .................... 00 16007

(51) Int. Cl.
*B01D 65/02* (2006.01)
*A01N 2/00* (2006.01)
(52) U.S. Cl. ............. 210/636; 210/321.71; 422/1; 422/20; 422/28; 422/40
(58) Field of Classification Search ............. 210/636, 210/645, 321.71, 321.6, 321.75, 321.69, 210/321.76, 321.7; 422/1, 20, 28, 40
See application file for complete search history.

(56) References Cited

U.S. PATENT DOCUMENTS
4,609,728 A 9/1986 Spranger et al.
(Continued)

FOREIGN PATENT DOCUMENTS
EP 0 315 420 A2 5/1989
(Continued)

OTHER PUBLICATIONS
(TORA) Toray Ind Inc., "Polymethyl Methacrylate Hollow Fibres of High Dimensional Stability Useful for Reverse Osmosis Membranes Prepared by Spinning in Aqueous Glycerol Mixture", Derwent Abstract of Japanese Appln. 50128773, (Oct. 11, 1975).
(Continued)

Primary Examiner—Ana Fortuna
(74) Attorney, Agent, or Firm—Finnegan, Henderson, Farabow, Garrett & Dunner, L.L.P.

(57) ABSTRACT

The present invention relates to a device for the extracorporeal treatment of blood or plasma, comprising two compartments, one compartment intended for circulating blood or plasma, and one compartment intended for circulating spent liquid, separated by a wet semi-permeable membrane, characterized in that the device has, before and after sterilization, the following technical characteristics:
the membrane is impregnated with an aqueous glycerol solution;
the aqueous glycerol solution contains from 7% to 15% by weight of glycerol and is free of toxic chemical compounds;
the two compartments are purged of the aqueous glycerol solution.

The present invention also relates to processes for manufacturing this device.

9 Claims, 3 Drawing Sheets

U.S. PATENT DOCUMENTS

| | | | |
|---|---|---|---|
| 4,720,343 A | * | 1/1988 | Walch et al. .......... 210/500.28 |
| 4,767,538 A | | 8/1988 | Jakubowski et al. |
| 4,833,200 A | * | 5/1989 | Noishiki et al. ........... 525/54.2 |
| 4,969,997 A | * | 11/1990 | Kluver et al. .......... 210/321.61 |
| RE34,239 E | | 5/1993 | Marze |
| 5,645,778 A | * | 7/1997 | Radovich et al. ............. 264/41 |
| 5,736,046 A | | 4/1998 | Althin et al. |
| 5,814,179 A | | 9/1998 | Ohmori et al. |
| 5,897,817 A | * | 4/1999 | Radovich et al. ............. 264/41 |
| 5,968,358 A | * | 10/1999 | Nizuka et al. ......... 210/500.23 |
| 6,077,443 A | | 6/2000 | Goldau |
| 6,090,048 A | | 7/2000 | Hertz et al. |
| 6,248,238 B1 | | 6/2001 | Burtin et al. |
| 6,423,323 B1 | * | 7/2002 | Neubourg ................... 424/401 |
| 6,596,167 B1 | * | 7/2003 | Ji et al. ................. 210/500.42 |

FOREIGN PATENT DOCUMENTS

| | | |
|---|---|---|
| EP | 0 564 053 | 10/1993 |
| EP | 0 630 655 A2 | 12/1994 |
| EP | 0 801 953 A1 | 10/1997 |
| EP | 0 847 796 A2 | 6/1998 |
| FR | 2 737 124 | 1/1997 |
| JP | 05192397 | 8/1993 |
| JP | 06-285162 | 10/1994 |
| JP | 06-296838 | 10/1994 |
| WO | WO 98/29478 | 7/1998 |

OTHER PUBLICATIONS (TEIJ) Teijin Ltd., Blood Treatment Device Sterilisation—by Subjecting Device with Dry Cellulose Acetate Semipermeable Fibrous Membrane to Gamma Rays Irradiation, Derwent Abstract of Japanese Appln. 59211459 A, (May 17, 1983).

* cited by examiner

APPARATUS FOR EXTRACORPOREAL BLOOD OR PLASMA TREATMENT COMPRISING A WET SEMI-PERMEABLE MEMBRANE AND METHODS FOR MAKING THE SAME

The present invention relates to a device for treating blood or plasma by extracorporeal circulation, comprising a wet semi-permeable membrane, and to processes for manufacturing this device.

Throughout this text, the expression "wet semi-permeable membrane" means a flat semi-permeable membrane or a bundle of hollow semi-permeable fibres, which contains at least 40% by weight of water, relative to the weight of the semi-permeable membrane. Also, throughout this text, the term "device" means a device for treating blood or plasma by extracorporeal circulation, which generally comprises two compartments separated by a semi-permeable membrane, each equipped with two access points, a first compartment being intended for circulating the patient's blood or plasma, and a second compartment being intended for circulating spent liquid. The two compartments of the device are also separated by the packaging mass, based on a suitable adhesive composition, intended to form, depending on the case:

- a cylindrical partition for separating the two compartments of a device whose membrane consists of a bundle of hollow fibres;
- or a leaktight seal in a device comprising a flat membrane.

Devices for treating blood or plasma by extracorporeal circulation are used in various medical or paramedical applications such as: treatment of renal insufficiency by dialysis or blood filtration, plasmapheresis and apheresis for therapeutic and non-therapeutic purposes, oxygenation of the blood, immunopurification, etc.

The present invention also relates to the use of an aqueous-glycerol solution to limit the risks of leakage and variations in the performance qualities of the wet semi-permeable structures made of polymer material, in particular to limit the variations in the water permeability of the wet semi-permeable membranes, over an acceptable range of values after the devices comprising these membranes have been subjected to a temperature below 0° C. for a period which may range from one day to more than one month. For example, this may arise during the cold seasons, during the transportation of the devices in transportation means that are not heated or are insufficiently heated. Under these conditions, various types of damage have been observed: in most cases, an undulation of the semi-permeable membranes, due to their elongation, associated with:

- a large decrease in the water permeability, which may be greater than or equal to 20% of the initial water permeability, or
- a loss of integrity of the device resulting from the appearance of holes in the semi-permeable membranes and/or detachments at the interface between the semi-permeable membranes and the packaging masses and/or cracks in the packaging masses, these types of damage generally leading to leakages of liquid between the two compartments.

In order to avoid the appearance of damage in the devices comprising wet semi-permeable membranes, when they are exposed to temperatures below 0° C., and also in order to prevent the growth of bacteria and moulds, it has been proposed, in Japanese patent application No. 629838 (KO-KAI) to fill the devices or to wet the semi-permeable membrane with an aqueous solution containing 20% to 80% by weight of glycerol (preferably from 30% to 70%) and containing from 5% to 40% by weight of an aliphatic alcohol.

The aliphatic alcohols recommended in the said application are methanol, ethanol, propanol and isopropanol, which have the drawback of being highly flammable. However, the devices thus treated cannot be sterilized by gamma-irradiation since this high-energy sterilization leads to the conversion of the abovementioned aliphatic alcohols into products such as aldehydes, which are toxic at the concentrations reached after this conversion.

The solution proposed in the said application is consequently not desirable in medical applications.

In addition, Japanese patent application No. 6296838 teaches that a glycerol concentration of less than 20% by weight in the aqueous solution claimed does not prevent this solution from freezing.

It is known practice to manufacture dry, glycerol-impregnated semi-permeable membranes, in order to protect them against radiation during sterilization by gamma-irradiation, and to prevent losses of water permeability. Needless to say, no damage to these membranes is observed in this case when they are exposed to temperatures below 0° C., since they contain little or no water.

It is also known practice to keep certain semi-permeable membranes wet by impregnating them with concentrated aqueous glycerol solutions (at least 40% by weight of glycerol) since they would otherwise irreversibly lose their water permeability and also their mechanical properties and would consequently become unusable in medical applications. Among the semi-permeable membranes that are stored in the wet state, mention may be made of those made of polyacrylonitrile.

Conventionally, before use, devices for the extracorporeal treatment of blood or plasma are degassed and rinsed with a sterile, apyrogenic aqueous sodium chloride solution. In the case of devices comprising dry glycerol-impregnated semi-permeable membranes or wet semi-permeable membranes impregnated with concentrated aqueous glycerol solutions, it is recommended to prolong the rinsing step in order to remove the air bubbles trapped in the inner channel of the membranes having the form of a bundle of fibres. In addition, on account of high glycerol contents in the membranes, it may occasionally be necessary to tap the devices to promote the degassing.

Glycerol is also known for its antifreeze properties. However, high concentrations of glycerol are required to lower the freezing point of water by a few degrees (Celsius), as may be seen on reading the table below, in which the freezing point of an aqueous glycerol solution has been given as a function of the amount of glycerol in the solution. These numerical data are extracted from the book entitled: "Handbook of Chemistry and Physics" 65th edition, CRC Press, 1975, page D-235.

| % of glycerol in the aqueous solution (by weight) | lowering of the freezing point of water (in ° Celsius) |
|---|---|
| 0.50 | 0.072 |
| 1.00 | 0.180 |
| 2.00 | 0.411 |
| 3.00 | 0.627 |
| 4.00 | 0.849 |
| 5.00 | 1.078 |

-continued

| % of glycerol in the aqueous solution (by weight) | lowering of the freezing point of water (in ° Celsius) |
|---|---|
| 6.00 | 1.316 |
| 7.00 | 1.561 |
| 8.00 | 1.811 |
| 9.00 | 2.064 |
| 10.00 | 2.323 |
| 12.00 | 2.880 |
| 14.00 | 3.469 |
| 16.00 | 4.094 |
| 18.00 | 4.756 |
| 20.00 | 5.46 |
| 24.00 | 7.01 |
| 28.00 | 8.77 |
| 32.00 | 10.74 |
| 36.00 | 12.96 |
| 40.00 | 15.50 |

Surprisingly, the Applicant has found that it is possible to limit the risks of leakage and variations in the water permeability of a device for the extracorporeal treatment of blood or plasma, comprising two compartments, one compartment intended for circulating blood or plasma, and one compartment intended for circulating spent liquid, separated by a wet semi-permeable membrane, when this device is subjected to a temperature below 0° C., for example –18° C., for a variable period of time which may range from one day to more than one month, if this device has, before and after sterilization, the three technical characteristics below:

the membrane is impregnated with an aqueous glycerol solution;

the aqueous glycerol solution contains from 7% to 15% by weight of glycerol and is free of toxic chemical compounds;

the two compartments are purged of the aqueous glycerol solution.

The solution developed in the context of the present invention for improving the cold-temperature resistance (temperature below 0° C., for example equal to –18° C.) of devices for the extracorporeal treatment of blood or plasma, comprising a wet semi-permeable membrane, leads to a result that is entirely surprising in the light of the knowledge provided by the abovementioned prior art.

Specifically, the aqueous solution according to the present invention, which is used to impregnate the semi-permeable membrane, contains a small amount of glycerol, from 7% to 15% by weight relative to the total weight of the solution, preferably from 8% to 12% by weight, these amounts being considered insufficient by the abovementioned prior art, in particular Japanese patent application No. 6296838 (KO-KAI) and the abovementioned data appearing in the book entitled "Handbook of Chemistry and Physics".

By virtue of the invention, the temperatures to which a device may be subjected without the appearance of any leaks between the compartments or a substantial variation in the water permeability, may be as low as –20° C., or may even be slightly lower than –20° C., when an aqueous glycerol solution containing from 10% to 15% by weight of glycerol is used.

The invention has several major advantages: firstly, the membrane impregnated with the aqueous glycerol solution containing from 7% to 15% by weight of glycerol is not damaged by a very high-energy sterilization, for instance sterilization by gamma-irradiation; secondly, the use of the device by the user is exactly identical to that of any device of the same type, the device moreover being easy to manipulate due to the fact that its two compartments are purged, and easy to rinse before use, when compared with a device of the same type comprising a glycerol-bearing membrane (at least 40% by weight of glycerol relative to the weight of the membrane); thirdly, the characteristics (blood compatibility, diffusive and convective transfer capacity, and capacity for protein adsorption) of the device subjected to a temperature below 0° C., for example equal to –10° C. or –18° C., for a variable period of time which may range from one day to more than one month, are not significantly impaired when compared with the same device stored at an ambient temperature above 0° C.

Advantageously, the minimum amount of aqueous glycerol solution represents 50% by weight relative to the total weight of the semi-permeable membrane.

In accordance with the invention, the aqueous glycerol solution is free of chemical compounds that are toxic or that become toxic after high-energy sterilization, such as gamma-irradiation. In particular, the aqueous glycerol solution is free of monohydric aliphatic alcohols, for instance methanol, ethanol, propanol and isopropanol. Also, the aqueous glycerol solution is free of chemical compounds that are toxic but known for their antifreeze properties such as, for example, ethylene glycol.

On the other hand, the aqueous glycerol solution can comprise one or more chemical compounds intended to treat the semi-permeable membrane in the bulk or at the surface to improve its biocompatibility: by way of example, mention may be made of polyethyleneimines (PEI), polyvinylpyrrolidones (PVP) and polyethylene glycols (PEG).

The chemical nature of the semi-permeable membrane of the device according to the invention is not critical. It may be based, for example, on polyacrylonitrile, polymethyl methacrylate, polysulphone, polyether sulphone, cellulose or polyamide.

The present invention is more particularly suitable for devices comprising a semi-permeable membrane which must be stored in a wet state, for instance membranes made of polyacrylonitrile or membranes made of polymethyl methacrylate.

Advantageously, the semi-permeable membrane is a flat membrane or a bundle of hollow fibres consisting of at least one polymer that is an acrylonitrile homopolymer or copolymer, this polymer preferably being electronegative. As examples of acrylonitrile copolymers that are suitable for the present invention, mention may be made of:

1) a copolymer of acrylonitrile and of at least one anionic or anionizable monomer containing, where appropriate, units derived from at least one other olefinically unsaturated monomer capable of being copolymerized with acrylonitrile, or 2) a copolymer of acrylonitrile and of at least one anionic or anionizable monomer and of at least one nonionic and non-ionizable monomer.

Some of these macromolecular compounds, and also the various monomers which may be selected as starting materials and their manufacture, are described in U.S. Pat. No. 4,545,910 regranted under No. Re. 34239.

Among these macromolecular compounds, those with which the medical device according to the invention is particularly suitable are defined above in (1). In particular, the invention is particularly suitable for compounds for which the anionic or anionizable comonomer is olefinically unsaturated and bears anionic groups chosen from sulphonate, carboxyl, phosphate, phosphonate and sulphate groups, and even more particularly when this comonomer is sodium methallyl sulphonate: this membrane, which is manufactured by the company Hospal and known under the trade name AN69, should be stored in the wet state, and generally contains about 70% by weight of water.

Needless to say, the precise nature of the counterion for the anionic groups is not essential for the correct functioning of the invention.

Among the olefinically unsaturated monomers capable of being copolymerized with acrylonitrile, mention may be made of alkyl acrylates, and in particular methyl acrylate.

The present invention is also suitable for devices comprising a semi-permeable membrane that has been treated in the bulk or at the surface, to improve its biocompatibility [such that the reactions (especially clotting) which take place when blood comes into contact with a foreign material do not take place, or take place only to relatively benign levels].

Examples Which may be Mentioned Include:
  the device described in European patent application No. 0 801 953 which comprises a semi-permeable membrane consisting of at least one electronegative polymer, in particular a polyacrylonitrile of the same type as those described above, treated in the bulk with an antiprotease and cationic agent, preferably nafamostat mesylate;
  the device described in European patent application No. 0 925 826, which comprises a semi-permeable membrane, based on polyacrylonitrile bearing fixed negative charges, treated with a neutral polymer such as polyvinylpyrrolidones (PVP) and polyethylene glycols (PEG), or with a cationic polymer, such as polyethyleneimines (PEI).

A subject of the invention is also a process for limiting the risks of leakage and variations in the water permeability of a device for the extracorporeal treatment of blood or plasma, which is subjected to a temperature below 0° C., this device comprising two compartments, one compartment intended for circulating blood or plasma, and one compartment intended for circulating spent liquid, separated by a wet semi-permeable membrane, the process comprising the steps of:
  preparing an aqueous glycerol solution containing from 7% to 15% by weight of glycerol and free of chemical compounds that are toxic before or after high-energy sterilization, such as gamma-irradiation;
  placing the aqueous glycerol solution in contact with the semi-permeable membrane;
  purging the device of the aqueous glycerol solution;
  sterilizing the device.

According to embodiment variants of the process according to the invention, the aqueous glycerol solution is placed in contact with the semi-permeable membrane by circulating this solution:
  in the compartment intended for circulating blood or plasma,
  or in the compartment intended for circulating spent liquid,
  or in the compartment intended for circulating blood or plasma and in the compartment intended for circulating spent liquid.

According to other embodiment variants of the process according to the invention:
  the aqueous glycerol solution contains from 8% to 12% by weight of glycerol,
  and/or the aqueous glycerol solution contains one or more chemical compounds intended to treat the semi-permeable membrane in the bulk or at the surface to improve its biocompatibility, preferably a chemical compound chosen from polyethyleneimines (PEI); as regards the amount of these chemical compounds to be included in the aqueous glycerol solution, reference may be made, for example, to the operating conditions listed in European patent application No. 0 925 826.

When the membrane is treated in the bulk or at the surface to improve its biocompatibility, the process according to the invention may be carried out with the steps of:
  preparing a solution containing one or more chemical compounds intended to improve the biocompatibility of the membrane;
  placing this solution in contact with the surface of the membrane intended to be placed in contact with blood or plasma;
  assembling the various components of the device, in particular mounting the membrane in a housing and producing the end pieces of this housing, if this assembly has not been performed before the first two steps mentioned above;
  preparing an aqueous glycerol solution containing from 7% to 15% by weight of glycerol and free of chemical compounds that are toxic before or after a high-energy sterilization, such as gamma-irradiation;
  placing the aqueous glycerol solution in contact with the semi-permeable membrane;
  purging the device of the aqueous glycerol solution;
  sterilizing the device.

If necessary, before placing the aqueous glycerol solution in contact with the semi-permeable membrane, the membrane is rinsed with water or an aqueous solution, for example an aqueous sodium chloride solution, in order to remove certain chemical compounds temporarily present in the membrane, that are useful for its manufacture and/or storage. This is the case, for example, for the membrane AN69 whose manufacture and storage involve the use of glycerol; in practice, the membrane AN69 is stored in the wet state and, to do this, is glycerol-treated by soaking in a water/glycerol mixture, usually in weight proportions corresponding to 40/60. In the context of the present invention, the membrane must consequently be deglycerolized before being impregnated with the aqueous glycerol solution containing from 7% to 15% by weight of glycerol. The rinsing operation in order to deglycerolize the membrane AN69 is performed by placing water or an aqueous solution, for example an aqueous sodium chloride solution, in contact with the membrane AN69. When the membrane AN69 is in the form of a bundle of hollow fibres, the rinsing operation is preferably performed by circulating water or an aqueous sodium chloride solution in the compartment intended for circulating blood or plasma.

Other characteristics and advantages of the invention will become apparent on reading the examples which follow. Reference may also be made to the attached drawings, in which.

EXAMPLES

Figure 1:
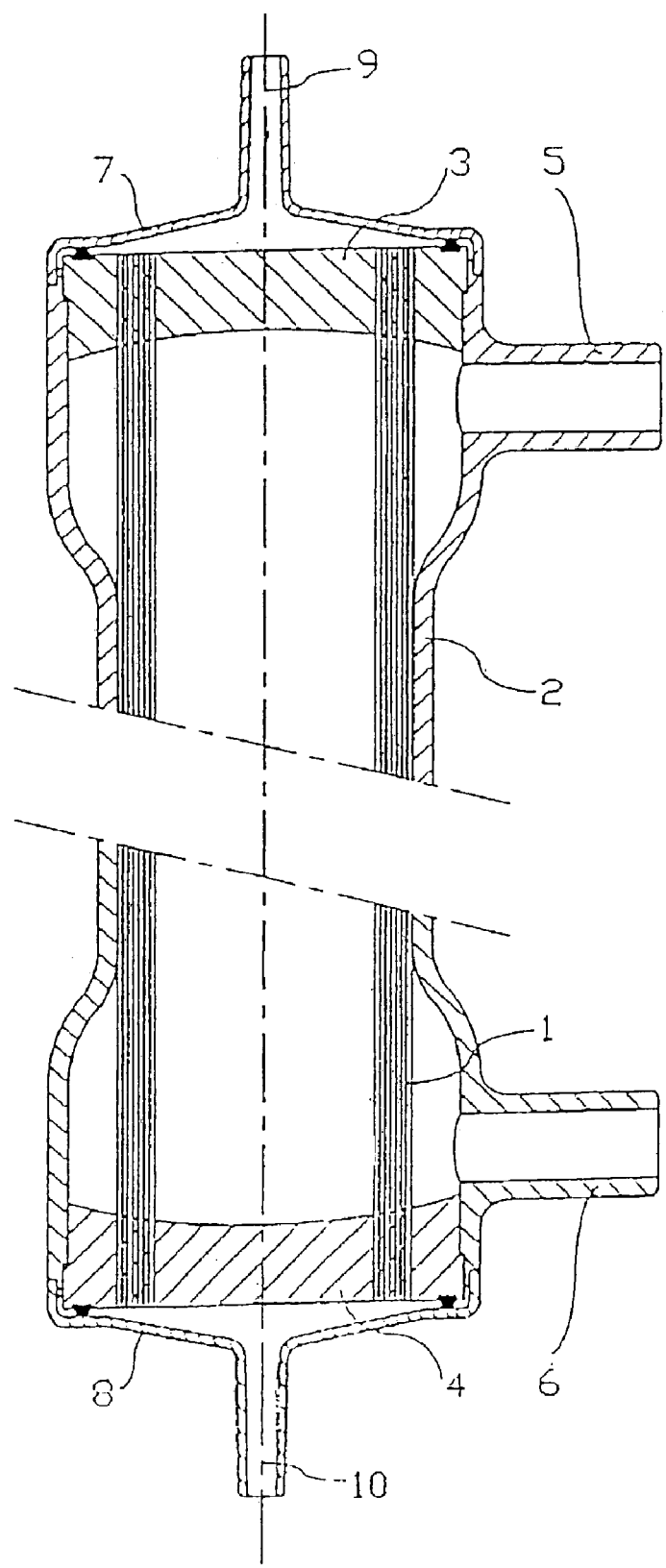
FIG. 1 represents a diagrammatic view in longitudinal cross section of a hollow-fibre dialyser.

A specific type of device for the extracorporeal treatment of blood, which is used to overcome renal insufficiency, has been used to illustrate the invention.

The type of device used in the examples is a blood dialyser/blood filter conventionally comprising two compartments separated by a semi-permeable membrane. A first compartment is intended to be connected by means of a removal tube and return tube to the patient's vascular system, whereas the second compartment has an inlet which may be connected to a source of dialysis fluid (treatment by blood dialysis and blood diafiltration) and an outlet connected to a means for removal of spent liquid (spent dialysate and/or ultrafiltrate). The membrane is chosen so as to allow diffusive and/or convective transfers of the metabolic waste products, from the blood compartment to the compartment for spent liquid. The membrane may be manufactured in the form of a flat membrane or a bundle of hollow fibres. A flat-membrane dialyser comprises a concertina-folded flat membrane band, an intercalating plate being introduced into all the folds opening on the same side. As may be seen in FIG. 1, a hollow-fibre dialyser comprises a bundle of hollow fibres 1, which is arranged in a tubular housing 2 in which it is securely fastened at its two ends by an adhesive disc, 3, 4. Besides linking the fibres together, the adhesive discs 3, 4 serve to delimit in the tubular housing 2 a leaktight compartment, to which access is gained by two tubes 5, 6 that are perpendicular to the axis of the housing 2. At each end of the housing 2 is fixed an end piece 7, 8 comprising an axial access tube 9, 10. The two tubes 9, 10 are symmetrical. The blood compartment of this device consists of the inner space delimited between each adhesive disc 3, 4 and the end piece 8, 9 closing the corresponding end of the tubular housing 2, and consists of the interior of the hollow fibres.

The semi-permeable membrane of the dialysers illustrated is a membrane AN69 in the form of a bundle of hollow fibres.

The main steps in the manufacture of a hollow fibre made of AN69 will now be briefly recalled. A polymer blend is prepared, containing 35% by weight of a copolymer of acrylonitrile and of sodium methallyl sulphonate, 52% by weight of dimethylformamide (DMF) and 13% by weight of glycerol. The polymer blend is heated to 130° C. and is extruded through a die with two concentric nozzles, nitrogen being injected into the inner nozzle to form the lumen of the hollow fibre. On contact with the ambient air (about 20–25° C.), the thermoreversible gel fibre leaving the die is the site of a heat phase inversion. The fibre is then received in a water bath in which the solvent (DMF) in the fibre is replaced with water. The fibre is then immersed in hot water at 95° C. where it is stretched to an order of fourfold. This is followed by a stabilization phase in hot water at 95° C. Finally, the fibre is glycerolized with a water/glycerol mixture, in 40/60 weight proportions.

In the examples which follow, the dialysers tested are dialysers (trade name Nephral 300, manufactured by Hospal Industrie, France), equipped with a bundle of AN69 hollow fibres with a working surface area of 1.3 m².

In accordance with the invention, to limit the risks of leaks and variations in the water permeability of theses dialysers when they are subjected to a temperature below 0° C., which may be as low as −20° C., the semi-permeable membrane is impregnated with a solution of demineralized water and glycerol containing from 7% to 15% by weight of glycerol, this solution being free of chemical compounds that are toxic or liable to become toxic after a high-energy sterilization, for instance sterilization by gamma irradiation. This impregnation step is performed after assembling the device, as represented in FIG. 1, after removing the glycerol required for the manufacture of the AN69 membrane and before sterilization.

Preferably, the semi-permeable membrane is impregnated by circulating the aqueous glycerol solution in the blood compartment: to do this, one of the tubes 9 (10) of the blood circuit is connected to a container containing the aqueous glycerol solution, the other access tube 10 (9) is connected to an empty receiving container, and the aqueous glycerol solution is made to circulate in the blood compartment, where appropriate.

In Examples 3 to 6 below, the precise conditions of the impregnation and of the following steps are:
1) circulation in the blood compartment (comprising the interior of the fibres) of 1 liter of water (flow rate of 200 ml/min) in order to rinse the semi-permeable membrane, in particular in order to remove the glycerol used for manufacturing the membrane;
2) circulation in the blood compartment of 2 liters of a solution of glycerol in demineralized water containing, depending on the case, 5, 10 or 15% by mass of glycerol, at a flow rate of 250 ml/min;
3) purging the dialyser compartments with air for about 30 seconds by imposing an air pressure of $5 \times 10^4$ Pa (0.5 bar) in the compartment intended for circulating spent liquid, and an air pressure of $3 \times 10^4$ Pa (0.3 bar) in the compartment intended for circulating blood;
4) leaktight closure of the access tubes 5, 6, 9 and 10 with stoppers;
5) sterilization by gamma-irradiation (25–36 kGy).

Examples 1 to 5

Assessment of the water permeability and leaktightness of Nephral 300 dialysers as a function of the storage time in a chamber regulated at a temperature of −10° C.

5 groups each comprising 10 Nephral 300 dialysers were assessed in Examples 1 to 5. The table below indicates the characteristics which differentiate each group of dialysers.

| Examples | Specific characteristics |
| --- | --- |
| 1 (control No. 1) | The 10 Nephral 300 dialysers are deglycerolized, not treated with an aqueous glyerol solution, and stored at an ambient temperature of about 20° C. |
| 2 (control No. 2) | The 10 Nephral 300 dialysers are deglycerolized, not treated with an aqueous glyerol solution, and stored at a temperature of −10° C. |
| 3 | The 10 Nephral 300 dialysers are deglycerolized, treated with an aqueous solution containing 5% by weight of glyerol, and stored at −10° C. |
| 4 | The 10 Nephral 300 dialysers are deglycerolized, treated with an aqueous solution containing 10% by weight of glyerol, and stored at −10° C. |
| 5 | The 10 Nephral 300 dialysers are deglycerolized, treated with an aqueous solution containing 15% by weight of glyerol, and stored at −10° C. |

In Examples 3, 4 and 5, the aqueous glycerol solution represents about 70% by weight of the membrane.

The weight percentage of glycerol in each membrane of the dialysers in Examples 3, 4 and 5 is, respectively, about 3.5%, 7% and 10.5%.

The water permeability of the dialysers in Examples 1 to 5 was measured after 7 days, 14 days and 28 days of storage, depending on the case, at −10° C. or at an ambient temperature of about 20° C. (Example 1: control No. 1).

It is recalled that the water permeability describes the amount of water which may be ultrafiltered through a semi-permeable membrane with a given active surface area, with a given transmembrane pressure over a given period of time. The conditions for measuring the water permeability in the examples are as follows:

flow rate of water in the compartment intended for circulating blood or plasma: 300 ml/min;
transmembrane pressure: 85 mmHg.

The average of the water permeability values measured in each group of dialysers was normalized by taking as the basis 100% of the average of the initial water permeability values of each group.

Figure 2:
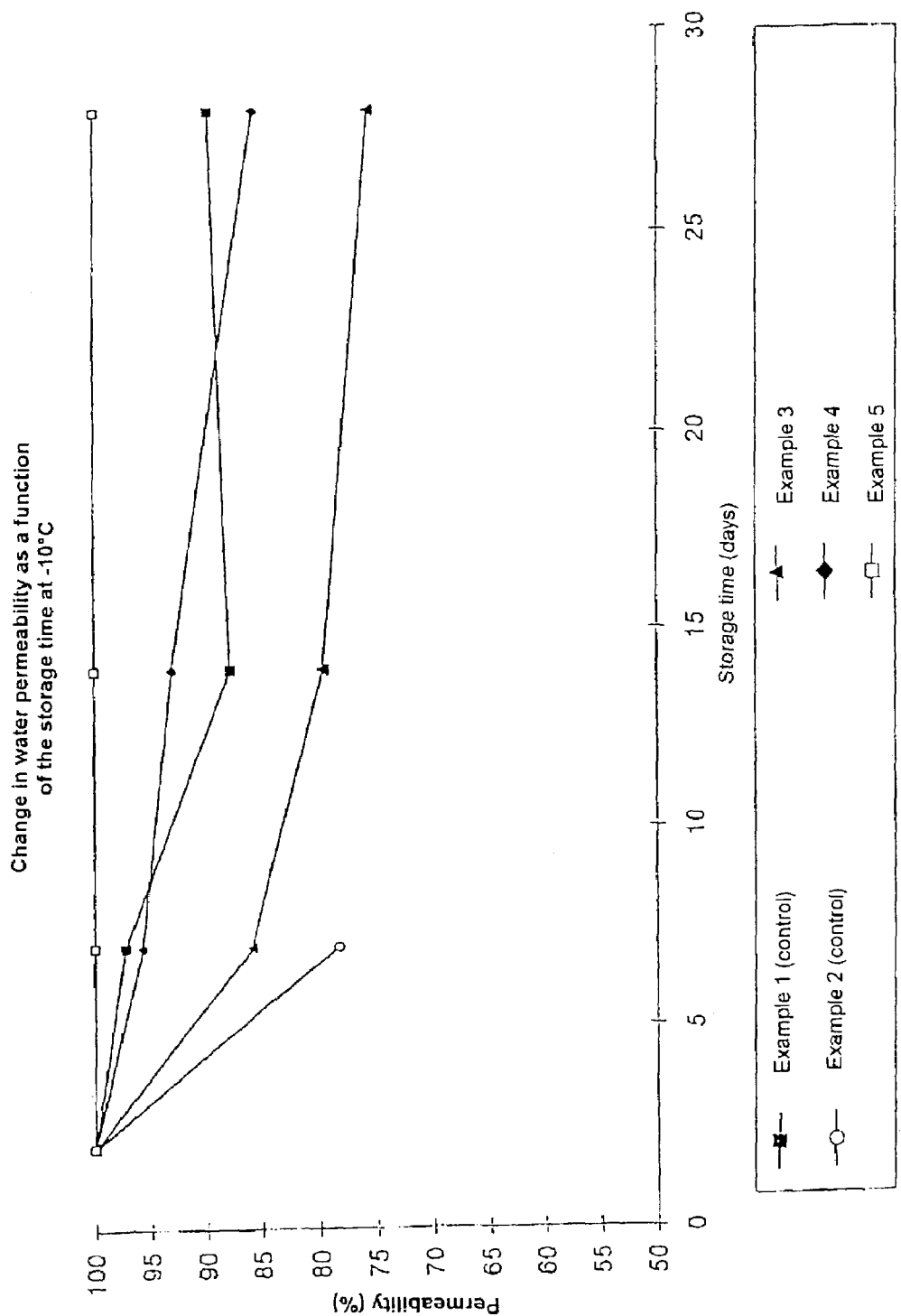
FIG. 2 shows the effect of the amount of glycerol in the aqueous solution used to impregnate the membrane AN69 on the appearance of leaks between the compartments of dialysers stored at −10° C.
Figure 3:
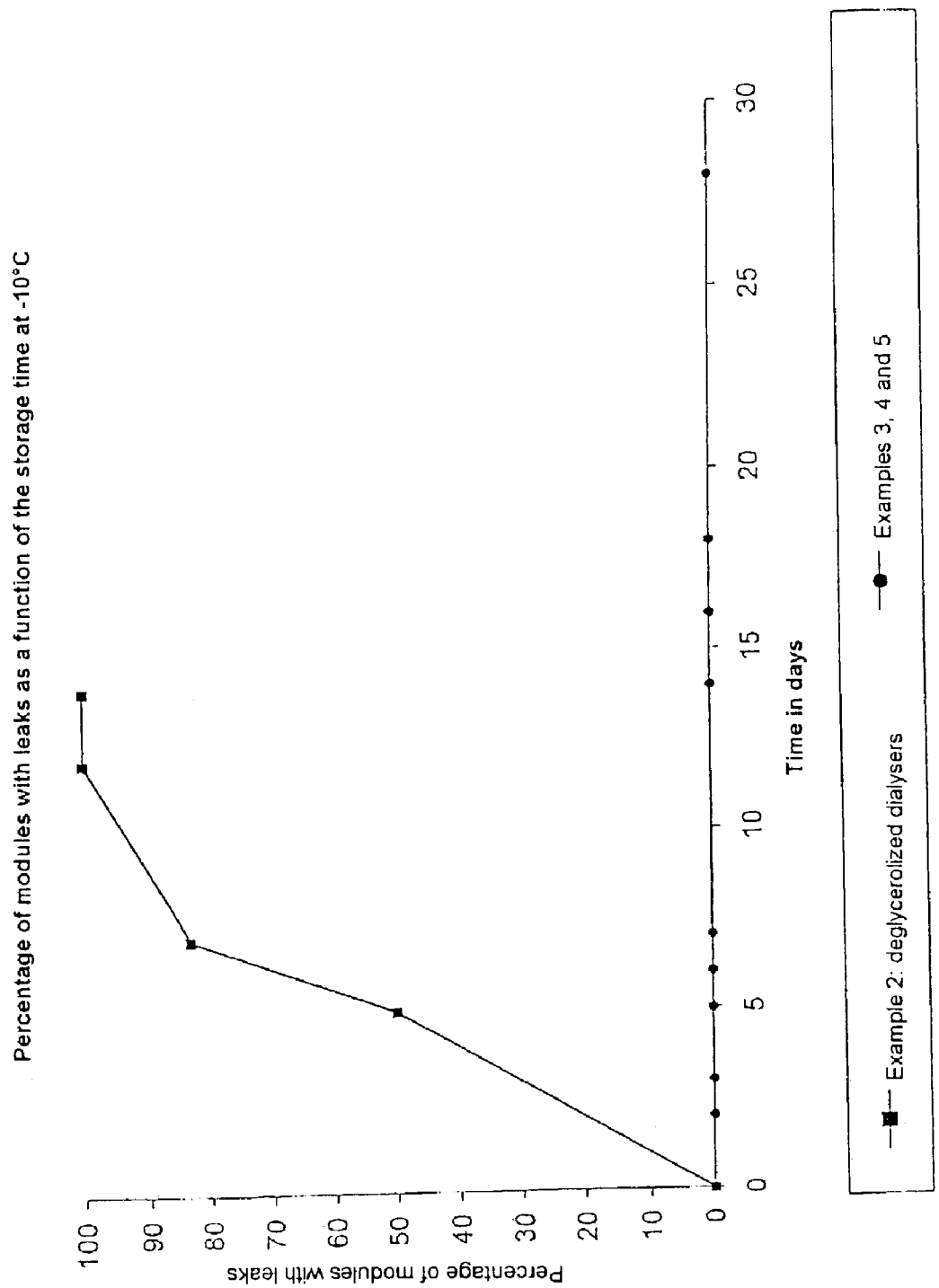
FIG. 3 shows the effect of the amount of glycerol in the aqueous solution used to impregnate the membrane AN69 on the water permeability of dialysers stored at −10° C.

The values obtained are given in FIG. 2 and reveal the water permeability losses (in %).

The dialysers of Example 5 (treatment with an aqueous solution containing 15% by weight of glycerol) are of noteworthy stability: no reduction in water permeability after 28 days at −10° C.

The dialysers of Example 4 (treatment with an aqueous solution containing 10% by weight of glycerol) show very good behaviour: the reduction in water permeability after 28 days at −10° C. is only 15%, and is very close to the reduction in water permeability of the deglycerolized dialysers, stored at ambient temperature (Example 1).

The dialysers of Example 3. (treatment with an aqueous solution containing 5% by weight of glycerol) are not stable: the reduction in the water permeability is 20% after 15 days at −10° C. and about 25% after 28 days at −10° C.

The dialysers of Example 2 (deglycerolized and stored at −10° C.) all show leaks after 7 days at −10° C.: macroscopic and microscopic observations of these dialysers revealed an elongation of the hollow fibres, cracks in the packaging adhesive, fibre/adhesive detachments and holes in the fibres.

Example 6—Storage at −18° C.

10 dialysers of deglycerolized Nephral 300 type are treated by circulating inside the fibres of each dialyser 2 liters of a solution containing 10% by mass of glycerol (flow rate of 250 ml/min). The liquid contained in the inner channel of the fibres is purged by circulation of air. The dialysers are stoppered in a leaktight manner and sterilized by gamma-irradiation. The dialysers are placed in a chamber regulated at a temperature of −18° C. After storage for one week, the dialysers are removed from the chamber. The leaktightness of the 10 dialysers was tested using an ATEQ device for pressurizing (under 1 bar) the compartment intended for circulating blood or plasma, the other compartment being open; the absence or otherwise of a drop in pressure at the outlet of the compartment intended for circulating blood or plasma is checked. The water permeability and the urea and vitamin B12 clearance were assessed on 3 dialysers of the series.

The operating conditions of the water permeability measurements are identical to those of Examples 1 to 5.

The operating conditions of the urea and vitamin B12 clearance measurements are as follows:

the dialyser is rinsed beforehand with 2 liters of physiological saline;

a dialysis bath is circulated in the compartment for spent liquid at a flow rate of 500 ml/min in an open circuit. The dialysis bath is an aqueous solution containing (in mmol/l): sodium: 135, potassium: 1.5, magnesium: 0.75, calcium: 1.75, chloride: 106.5, acetate: 35;

a dialysis bath containing 1 g/l of urea and 100 mg/l of vitamin B12 is circulated in the blood compartment, in a closed circuit. The volume of dialysis bath is equal to 2 liters and is kept constant by supplying solution at a flow rate of 10 ml/min, in order to compensate for the ultrafiltration. The flow rate of the dialysis bath is equal to 200 ml/mn;

the ultrafiltration is set at a flow rate of 10 ml/min;

after 30 min, the urea and vitamin B12 concentrations at the inlet and outlet of the blood compartment are determined.

The clearance, which represents the level of purification of the dialyser, is expressed as:

$$\text{clearance} = [(QBI \times CBI) - (QBI \times CBO)]/CBI$$

with: QBI=flow rate at the blood compartment inlet
CBI=concentration at the blood compartment inlet
CBO=concentration at the blood compartment outlet

| Dialyser | Leaktight-ness | Water permeability ml/h m² mmHg | Urea clearance ml/min | B12 clearance ml/min |
|---|---|---|---|---|
| 6a | yes | 40.8 | 218 | 90 |
| 6b | yes | 46.4 | 236 | 111 |
| 6c | yes | 53.2 | 236 | 112 |
| 6d to 6j | yes | nm* | nm | nm |

*nm means not measured

Given that:
the permeability of the dialysers of Example 6 must be greater than 35.4 ml/h m² mmHg,
the initial urea clearance values of the dialysers of Example 6 range from 210 to 256 ml/min,
the initial vitamin B12 clearance values of the dialysers of Example 6 range from 90 to 134 ml/min, the correct behaviour of these dialysers after storage for one week at −18° C. is observed.

The invention claimed is:

1. A process for limiting risks of leakage and variations in a water permeability of a device for the extracorporeal treatment of blood or plasma, said device being subjected to a temperature below 0° C., and comprising, a first compartment configured to circulate blood or plasma, and a second compartment configured to circulate spent liquid, said first and second compartments being separated by a semi-permeable membrane, said semi-permeable membrane being stored in a wet state, said process comprising the steps of:
preparing an aqueous glycerol solution having a concentration of 7% to 15% by weight of glycerol and being free of chemical compounds that are toxic before or after high-energy sterilization;
placing the aqueous glycerol solution in contact with the semi-permeable membrane;
purging the device of the aqueous glycerol solution; and
sterilizing the device with higher energy sterilization.

2. A process according to claim 1, wherein the step of placing the aqueous glycerol solution in contact with the semi-permeable membrane by circulating the aqueous glycerol solution in the first compartment.

3. A process according to claim 1, wherein the step of placing the aqueous glycerol solution in contact with the semi-permeable membrane by circulating the aqueous glycerol solution in the second compartment.

4. A process according to claim 1, wherein the step of placing the aqueous glycerol solution in contact with the semi-permeable membrane by circulating the aqueous glycerol solution in the first compartment and the second compartment.

5. A process according to claim 1, wherein said high-energy sterilization includes exposure of said aqueous glycerol solution to gamma irradiation.

6. A process for limiting risks of leakage and variations in a water permeability of a device for extracorporeal treatment of blood or plasma, said device being subjected to a temperature below 0° C., and comprising, a first compartment configured to circulate blood or plasma, and a second compartment configured to circulate spent liquid, said first and second compartments being separated by a semi-permeable membrane, said semi-permeable membrane being stored in a wet state, said process comprising the steps of:
   preparing a solution having one or more chemical compounds, said one or more chemical compounds improving the biocompatibility of the membrane;
   placing said solution in contact with a surface of the membrane, said surface being configured to be placed in contact with blood or plasma;
   mounting the membrane with improved biocompatibility in a housing;
   preparing an aqueous glycerol solution having a concentration of glycerol from 7% to 15% by weight and being free of chemical compounds that are toxic before or after a high-energy sterilization;
   placing the aqueous glycerol solution in contact with the semi-permeable membrane;
   purging the device of the aqueous glycerol solution; and
   sterilizing the device with higher energy sterilization.

7. A process according to claim 6, wherein said high-energy sterilization includes exposure of said aqueous glycerol solution to gamma irradiation.

8. A process for limiting risks of leakage and variations in a water permeability of a device for extracorporeal treatment of blood or plasma, said device being subjected to a temperature below 0° C., and comprising, a first compartment configured to circulate blood or plasma, and a second compartment configured to circulate spent liquid, said first and second compartments being separated by a semi-permeable membrane, said semi-permeable membrane being stored in a wet state, said process comprising the steps of:
   mounting the membrane in a housing;
   preparing a solution having one or more chemical compounds, said compounds improving a biocompatibility of the membrane;
   placing said solution in contact with a surface of the membrane, said surface being configured to be placed in contact with blood or plasma;
   preparing an aqueous glycerol solution having a concentration of glycerol from 7% to 15% by weight and being free of chemical compounds that are toxic before or after a high-energy sterilization;
   placing the aqueous glycerol solution in contact with the semi-permeable membrane;
   purging the device of the aqueous glycerol solution; and
   sterilizing the device with higher energy sterilization.

9. A process according to claim 8, wherein said high-energy sterilization includes exposure of said aqueous glycerol solution to gamma irradiation.

* * * * *

UNITED STATES PATENT AND TRADEMARK OFFICE
CERTIFICATE OF CORRECTION

| | | |
|---|---|---|
| PATENT NO. | : 7,077,961 B2 | Page 1 of 1 |
| APPLICATION NO. | : 10/203106 | |
| DATED | : July 18, 2006 | |
| INVENTOR(S) | : Michel Thomas | |

It is certified that error appears in the above-identified patent and that said Letters Patent is hereby corrected as shown below:

On the title page, item (30), "Dec. 18, 2000" should read --Dec. 8, 2000--.

Signed and Sealed this

Nineteenth Day of September, 2006

JON W. DUDAS
*Director of the United States Patent and Trademark Office*